(12) United States Patent
Brechbuehler et al.

(10) Patent No.: US 8,177,745 B2
(45) Date of Patent: May 15, 2012

(54) NEEDLE SAFETY MODULE COMPRISING A LOCKING MECHANISM AND A USER IDENTIFICATION

(75) Inventors: Jonas Brechbuehler, Muensingen (CH); Christian Gratwohl, Aarau (CH); Marc Lanz, Lobsigen (CH); Urs Widmer, Bern (CH); Martin Wymann, Liebefeld (CH)

(73) Assignee: TecPharma Licensing AG, Burgdorf (CH)

( * ) Notice: Subject to any disclaimer, the term of this patent is extended or adjusted under 35 U.S.C. 154(b) by 276 days.

(21) Appl. No.: 12/392,827

(22) Filed: Feb. 25, 2009

(65) Prior Publication Data

US 2009/0259178 A1     Oct. 15, 2009

Related U.S. Application Data

(63) Continuation of application No. PCT/CH2007/000412, filed on Aug. 22, 2007.

(30) Foreign Application Priority Data

Sep. 1, 2006 (DE) .......................... 10 2006 041 128

(51) Int. Cl.
*A61M 5/00* (2006.01)
(52) U.S. Cl. ....................................................... 604/110
(58) Field of Classification Search .................. 604/110, 604/111, 192, 198, 263
See application file for complete search history.

(56) References Cited

U.S. PATENT DOCUMENTS

| | | | |
|---|---|---|---|
| 5,338,310 A * | 8/1994 | Lewandowski | 604/192 |
| 6,855,129 B2 * | 2/2005 | Jensen et al. | 604/110 |
| 7,001,364 B1 * | 2/2006 | Farhi | 604/198 |
| 2003/0014018 A1 | 1/2003 | Giambattista et al. | |
| 2005/0113750 A1 | 5/2005 | Targell | |

FOREIGN PATENT DOCUMENTS

| | | |
|---|---|---|
| EP | 1 557 191 A2 | 7/2005 |
| WO | 92/09319 A1 | 6/1992 |
| WO | 01/91837 A1 | 12/2001 |
| WO | 03/105935 A2 | 12/2003 |
| WO | 2004/071560 A1 | 8/2004 |
| WO | 2006/082350 A1 | 8/2006 |

* cited by examiner

*Primary Examiner* — Christopher D Koharski
(74) *Attorney, Agent, or Firm* — Dorsey & Whitney LLP; David E. Bruhn, Esq.

(57) ABSTRACT

A needle safety module for being connected to an injection device for administering a liquid product to a patient, the module including a housing, a needle connected to the housing, and a needle protective sleeve having one end which can be placed on an injection point of the patient and displaced axially in relation to one of the needle or the housing from a starting position in which the needle tip is covered to an injection position in which the needle tip at least touches the injection point, the needle protective sleeve lockable in relation to one of the needle or the housing.

20 Claims, 11 Drawing Sheets

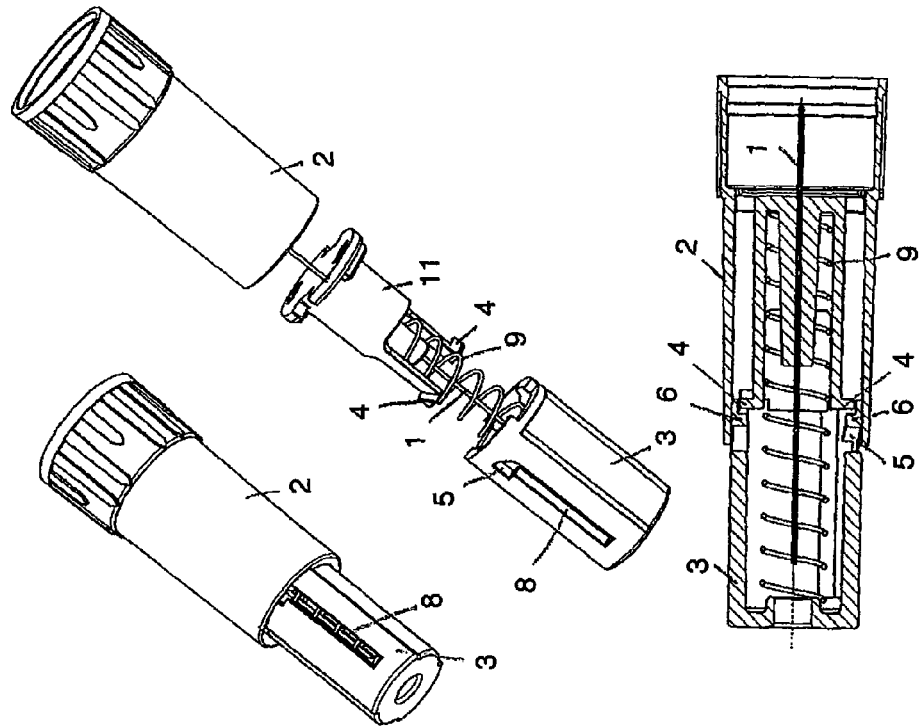
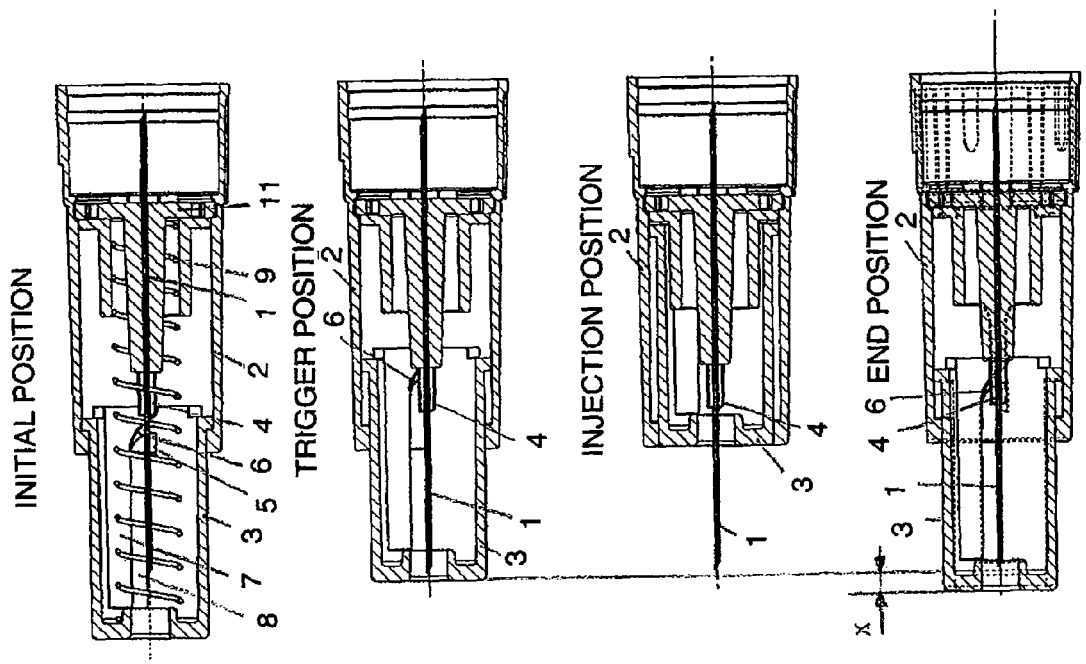
Fig. 2

SECTION A-A

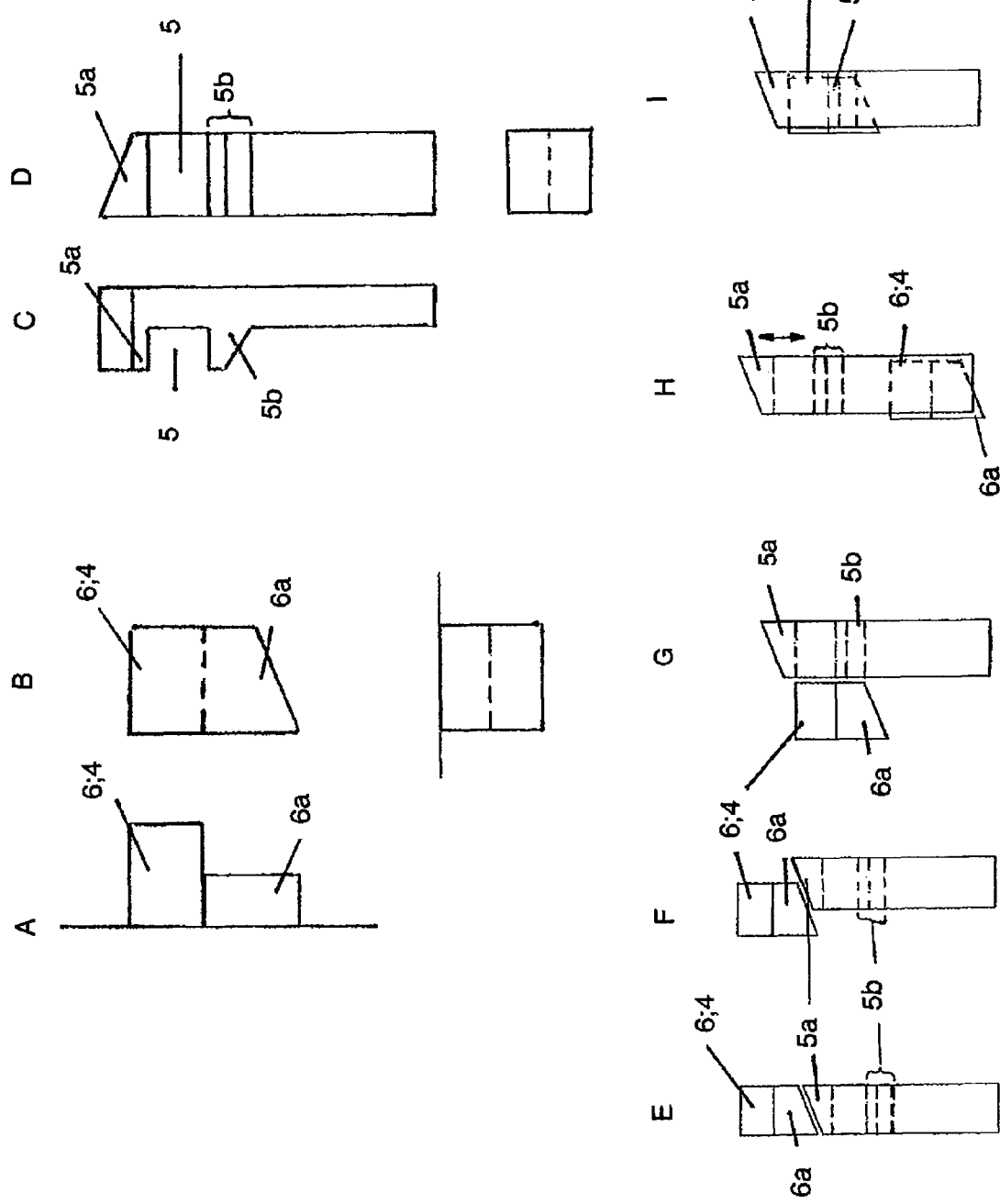

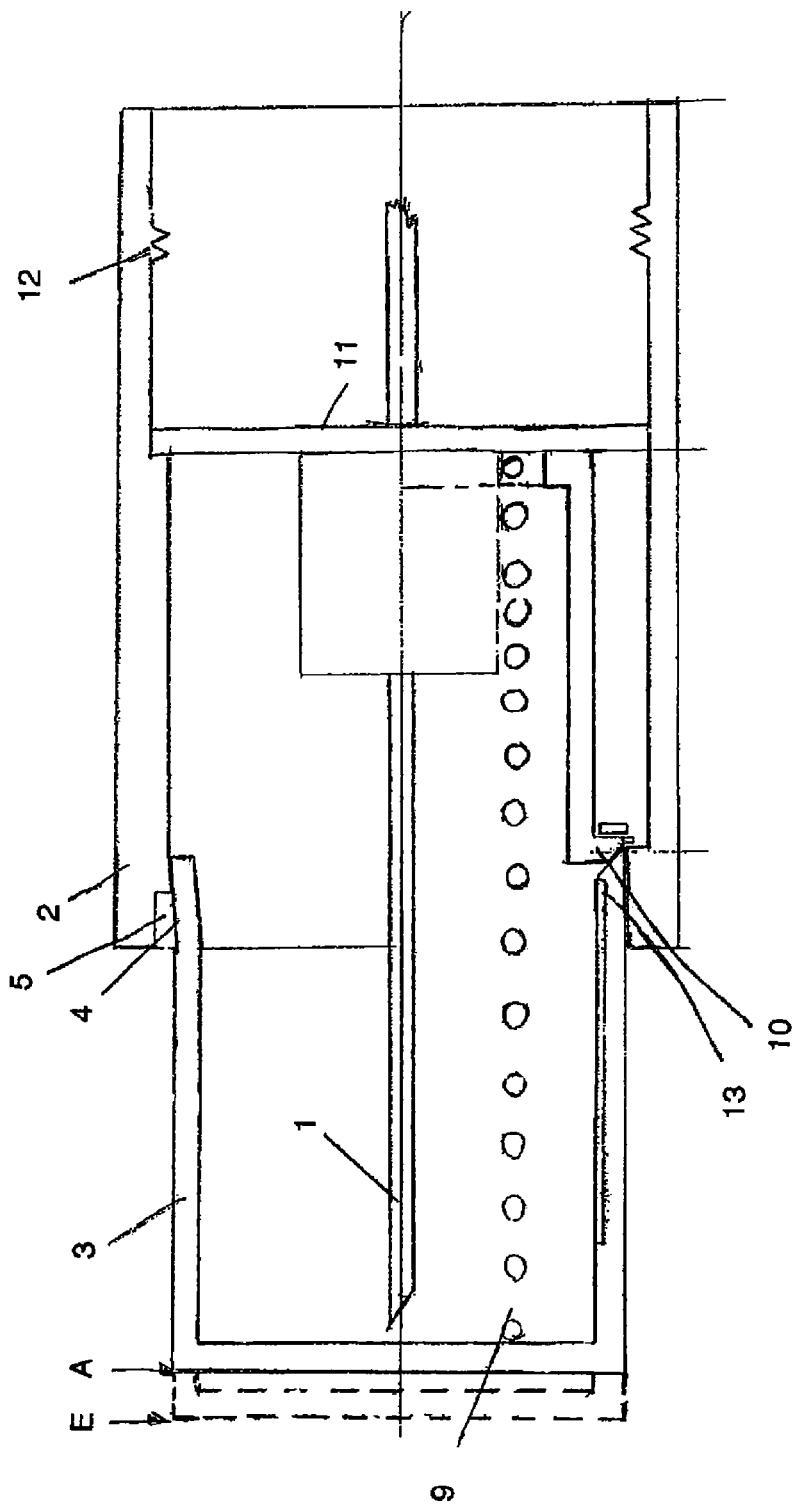
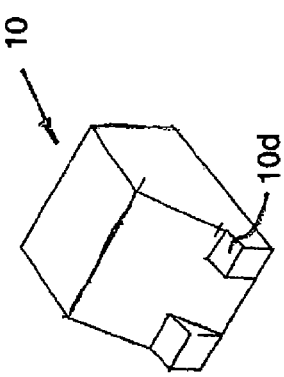
Fig. 8

NEEDLE SAFETY MODULE COMPRISING A LOCKING MECHANISM AND A USER IDENTIFICATION

CROSS-REFERENCED RELATED APPLICATIONS

This application is a continuation of International Patent Application No. PCT/CH2007/000412 filed Aug. 22, 2007, which claims priority to German Patent Application No. DE 10 2006 041 128.5 filed Sep. 1, 2006, the entire content of both of which is incorporated herein by reference.

BACKGROUND

The present invention relates to device for injecting, infusing, administering, dispensing or delivering a substance, and to methods of making and using such devices. More particularly, the present invention relates to a needle safety module which can be attached to an injection device, e.g. an injection pen or so-called automatic injectors. A product or substance contained in the injection device, such as a liquid medicament, can be administered to a patient by or via the safety module. In some embodiments, the present invention relates to a mechanism designed to enable safe handling of a needle and, in some embodiments, to a code by or from which it is possible to tell whether a needle has been used.

Needle safety modules typically comprise a housing in which a needle is accommodated so that it is axially immobile. The housing can be attached to an injection device. The needle is surrounded by a needle guard before and after an injection so that the user of the safety module can not pierce himself with the needle. In addition to being painful, inadvertent piercing can lead to infections, such as HIV or hepatitis. For an injection, the needle guard is placed on the desired injection point and pushed back into an injection position by pressing the needle guard against the injection point, causing the needle to pierce the injection point. Once the needle has been pulled out, the needle guard is pushed back far enough over the needle to cover it, for example by a spring. In most instances, the needle is to be used only once.

U.S. Pat. No. 6,855,129 B2 discloses a needle safety module which is designed so that once the needle safety module has been used, a needle guard is prevented from moving axially. The mechanism has a locking sleeve which is initially guided by a housing as the needle guard is pushed back in the proximal (rearward) direction. Once the guided movement is complete, the locking sleeve is rotated by the needle guard as the needle guard continues to be pushed backward. This rotating movement continues as the needle guard is moved in the distal direction due to projections disposed on the housing and recesses in the proximal end of the needle guard until a projection of the locking sleeve locates in a lock element formed by the housing. As a result, the needle guard is prevented from moving any farther in the distal direction. The housing has an opening, through which the projection of the locking sleeve can be seen when the locking sleeve is engaged with the housing in a locked arrangement.

SUMMARY

One object of the present invention is to provide a needle safety module which offers a simple, reliable way of preventing a needle guard from being pushed back again, i.e. to expose or reveal the needle, after an injection. Another object of the present invention is to provide a needle safety module which makes it easier to tell whether the module, and needle therein, has already been used.

In one embodiment, the present invention comprises a needle safety module for being connected to an injection device for administering a liquid product or substance to a patient, the module including a housing, a needle connected to the housing, and a needle protective sleeve having one end which can be placed on an injection point of the patient and displaced axially in relation to one of the needle or the housing from a starting position in which the needle tip is covered to an injection position in which the needle tip at least touches the injection point, the needle protective sleeve lockable in relation to one of the needle or the housing.

In one embodiment, the present invention comprises a needle safety module for fixing to an injection device for administering a liquid product wherein the module comprises a housing, a needle that is connected in an axial manner to the housing, a needle protective sleeve, the distal end of which can be inserted onto an injection point and can be displaced axially in relation to the needle or the housing from a starting position in which the distal needle tip is covered to an injection position in which the distal end protrudes as far as the needle protective sleeve such that the distal needle tip touches at least the injection point in an end position in which the distal needle tip is covered, and wherein the needle protective sleeve is locked in an axial manner in its end position in relation to the needle or to the housing.

In one embodiment, a needle safety module in accordance with the present invention comprises a housing connected to an injection needle so that the needle is axially immobilized. The housing comprises a sleeve-like, cylindrical main part and a needle holder which form the housing when assembled. The injection needle may be connected to the needle holder or, in the case of a one-part housing, to the housing. Injection moulding processes are suitable for this purpose, by which plastic is cast around the needle. The sleeve-like housing or housing part may be attached to the distal (forward or front) end of an injection device. To this end, the housing may be provided with an appropriate fixing structure or feature, such as a screw, snapper or catch connection (e.g. snap-fit or click-fit connection). The needle may project out from the needle holder in the proximal direction so that when the needle safety module is attached to an injection device, the proximal end of the needle pierces a septum of a product container, thereby establishing a flow connection to the interior of the product container. The needle projects so far from the needle holder in the proximal direction that it is still laterally surrounded by the sleeve-shaped housing and does not project beyond the proximal end of the housing.

In some embodiments, the housing may be used to mount a needle guard so that it is able to slide relative to the housing. The needle guard may be mounted so that it can not rotate relative to the housing but is able to slide axially. While, in some embodiments, a non-rotating arrangement is preferred, it is not necessary. The needle guard is pushed in the distal direction by a spring or more generally an elastic means supported on the housing, e.g. on the needle holder and on the needle guard. For example, the needle guard may be closed at its distal end with the exception of a small orifice, the purpose of the orifice being to allow the needle to be extracted from the distal end of the needle guard. The spring is supported on the end face of the needle guard and on the needle holder of the housing. The needle guard can be placed on or against an injection point of a patient by its distal end or distal end face.

In some embodiments, the needle guard can be moved from an initial position via an injection position into an end position. The length by which the needle guard extends out from the housing in the distal direction and the length by which the needle extends out from the needle holder in the distal direction are adapted to one another so that the needle tip does not extend out from the needle guard in the initial position and in the end position. This rules out the possibility of a user of the device piercing himself with the distal needle tip when the needle guard is in the initial position and the end position. When the needle guard is in the injection position, the needle tip extends out from the needle guard far enough for the distal needle tip to at least touch the injection point and, in some embodiments, pierce the patient. In some embodiments, there is no possibility of the needle guard moving into its initial position when the distal needle tip is at least touching the injection point and, in some embodiments, the needle guard can only be pushed in the distal direction into an end position once the distal needle tip is touching the injection point. A so-called "early-triggering" needle safety module of this type rules out the risk of being infected with contagious germs because as soon as the needle tip has made contact with the body tissue of a first patient, the needle guard can only be moved into an end position. In the end position, the needle guard is locked so that it can not move axially relative to the needle or to the housing. This rules out any possibility of a second patient being infected by the needle tip, which might have been infected due to contact with the first patient.

In one aspect of the present invention, it is assumed that the needle guard is displaced by a specific distance measured in the direction in which the needle guard is moved between its initial position and its end position. This displacement enables the user to tell whether the needle safety module can still or can no longer be used. In some preferred embodiments, the needle guard is displaceable in the distal or proximal direction from its initial position into its end position. The needle guard may have one or more markings, for example, which can be seen when the needle guard is in the initial position or in the end position. A marking may be a colored marking or a symbol, a word or a character. The marking may be strip-shaped, for example, and extend around the circumference, for example ring-shaped. The marking may be disposed on the needle guard in the region of the distal end of the housing or in the region of an orifice or window of the housing so that the marking is visible when the needle guard is in the initial position or in the end position. When the marking is not visible, depending on the position of the needle guard, it may be covered by the housing.

If the marking is disposed on the needle guard in the region of the distal end of the housing in the case of a needle guard that is displaced in the proximal direction from the initial position to the end position, the marking will be visible in the initial position but will not be visible in the end position. Alternatively or in addition, a marking may be visible through the window in the initial position and not visible in the end position or vice versa.

If the needle guard is moved in the distal direction from the initial position to the end position, the marking, which is disposed on the needle guard in the region of the distal end of the housing, is not visible when the needle guard is in the initial position and visible in the end position. Alternatively or in addition, a marking may not be visible through the window in the initial position and visible in the end position, or vice versa.

The advantage of these designs is that a user can easily and reliably tell whether the needle guard is in the initial position or in the end position, in other words whether the needle safety module can still be used or has already been used.

In another embodiment of the present invention, the needle guard has a first marking which is visible when the needle guard is in an initial position and a second marking different from the first which is visible in an end position. In some preferred embodiments, the second marking is covered when the needle guard is in the initial position and the first marking is covered when the needle guard is in the end position.

For example, in the case of a needle guard which is moved in the proximal direction from the initial position to the end position, the following will apply: the first marking may be disposed on the needle guard in the region of the distal end of the housing and the second marking may be disposed on the needle guard in the region of a window, in which case the first marking is visible in the initial position and the second marking is visible in the end position, or vice versa. As an alternative or in addition, a first and a second marking may be provided in the region of the window, for example.

For example, in the case of a needle guard which is displaced in the distal direction from the initial position to the end position, the following will apply: the first marking may be disposed on the needle guard in the region of the distal end of the housing and the second marking may be disposed in the region of a window, in which case the first marking is visible in the end position and the second marking is visible in the initial position, or vice versa. As an alternative or in addition, a first and a second marking may be provided in the region of the window, for example.

By way of example and with a view to providing a clearer understanding, a marking which is visible when the needle guard is in the initial position may be green and a marking which is visible when the needle guard is in the end position may be red.

In a second aspect of the present invention, a lock element is provided on one of the needle guard and housing and a complementary lock element is provided on the other of the needle guard and housing, wherein in the end position, the lock element latches into the complementary element. In some preferred embodiments, the lock element is a projection or a cam and the complementary element may be a recess, which may be formed by or between two projections. The lock element or the complementary element may be disposed on a flexible, e.g. elastic and/or resilient arm(s) so that the lock element or complementary element can effect a latching movement. In some preferred embodiments, only one of the lock element and complementary element is disposed on such an arm. In some preferred embodiments, the lock element and the complementary element may be formed integrally on the needle guard or housing or needle holder.

In some preferred embodiments, the needle safety module has an activation cam, which, as the needle guard is being moved in the proximal direction out of the initial position, pushes the lock element or complementary lock element transversely to the direction of movement so that the lock element or complementary element can be moved past the activation cam. The activation cam may be formed on the element on which the lock element or complementary element is formed, e.g. on the housing or needle guard. In some embodiments, the lock element or complementary element touches the activation cam or slides along it as it moves past it. For example, when the needle guard is in the initial position, the lock element or complementary element may be disposed so far in front of the activation cam that the distance between the lock element or complementary element and the activation cam is shorter than the total distance to the needle guard. For example, the lock element or complementary element may touch the activation cam when the needle guard is in the initial position. The purpose of the activation cam is to prevent the lock element or complementary element from being returned to a position in front of the activation cam once the lock element or complementary element has moved past the activation cam, so that the needle guard is no longer able to move back into its initial position. In some preferred embodiments, a marking of the type explained above may have a maximum width extending in the direction of the longitudinal axis which corresponds to the distance which the lock element or complementary element must travel to move past the activation cam. Due to the relatively short distance which the needle guard must travel to move the lock element or complementary element past the activation cam, a needle safety module of this design may be referred to or thought of as "early triggering."

In some preferred embodiments, the lock element or complementary element is moved past the activation cam as soon as the needle tip has made contact with the injection point so that the needle guard is guided into the end position during the movement in the distal direction and can no longer be moved into the initial position. Having moved past the activation cam, the lock element or complementary element snaps back in the direction from which it was deflected by the activation cam. For example, when the lock element or complementary element snaps back, it has moved past the activation cam.

In some preferred embodiments, the activation cam is disposed in an axial position such that the lock element or complementary element is moved past the activation cam at the latest when the distal needle tip is able to make contact with the injection point. In some embodiments, the needle length may also be adapted as a function of the axial position of the activation cam or vice versa.

In some embodiments, the activation cam is shaped so that the lock element or complementary element is pushed by the activation cam transversely to the direction in which the needle guard is moved as the needle guard is being moved in the distal direction away from a position in which the lock element or complementary element is moved past the activation cam. E.g., the lock element or complementary lock element is able to engage due to the movement transversely to the movement direction. The activation cam may have oblique surfaces or curves so that the lock element or complementary element is moved by the activation cam transversely to the direction of movement of the needle guard as the needle guard is being moved. The movement transversely to the direction of movement may be a movement in the radial direction or in the circumferential direction, e.g. at a tangent to the circumferential direction of the needle guard or housing.

In one preferred embodiment, the activation cam may serve as a lock element, in which case when the needle guard is moved in the distal direction from a position in which the complementary element is moved past the activation cam, the complementary element latches in the activation cam. The connections described here, which are established when the lock element is disposed in the complementary element, are designed so that they can not be released by a force applied to the needle guard in the distal or proximal direction without breaking the needle safety module.

In another preferred embodiment, the lock element or complementary lock element is disposed outside of, to the side, in front of or behind an alignment running through the activation cam extending in the direction of movement of the needle guard.

In yet another embodiment of the present invention, as an alternative to or in addition to the descriptions and explanations given above, it may be advantageous to provide a locking element which is displaceable relative to the housing and the needle guard, which in an initial position engages with the needle guard and the housing and blocks or prevents a movement of the needle guard only in the distal direction. The locking element may be of an integral design with the housing or needle holder, for example. Alternatively, the locking element may be an additional part, which is able to slide along the needle holder or is fitted on the needle holder prior to using the needle safety module. For example, the locking element may be integrally joined to the housing, needle holder or a part adjoining the needle holder by a flexible, e.g. an elastic, arm. The locking element may have at least one lock lug acting in the distal direction, which is supported on a shoulder in the housing. Due to the fact that the locking element is able to extend through the wall of the needle guard, a movement of the needle guard in the distal direction is blocked from the initial position.

In some preferred embodiments, the needle guard is designed so that when the needle guard moves in the proximal direction, the locking element is moved out of engagement with at least the housing, as a result of which the needle guard can be moved by a movement in the distal direction into the end position in which the needle guard is disposed distally of the initial position. In some embodiments, the needle guard and/or the locking element may be adapted to one another and/or have driving surfaces or ramps adapted to one another so that the movement of the needle guard is converted into a transverse movement of the locking element. In some preferred embodiments, the locking element is displaceable transversely to the direction of movement of the needle guard. After the transverse movement of the locking element, the locking element may still be engaged with the needle guard or may have engaged with the needle guard again. Having moved out of engagement with the housing, the locking element latches with the needle guard, wherein the locking element is at least partially slaved in the movement of the needle guard in the proximal or in the distal direction. For example, once the needle guard has been pushed in the proximal direction, the locking element is moved out of engagement with the housing and needle guard, then latches in the housing and is then driven by the needle guard in the distal direction as the needle guard moves back in the distal direction. In the end position, namely when the needle guard is in a position disposed distally of the needle guard when in its initial position, the lock element provided on the needle guard can then engage with the complementary lock element formed by the housing so that the needle guard and housing latch and are axially fixed.

It should be understood that the first and second aspects or any embodiments of the present invention may complement one another and may therefore be combined with one another.

BRIEF DESCRIPTION OF THE DRAWINGS

FIGS. 2 to 3F are views of another embodiment of a needle safety module in accordance with the present invention;

FIG. 7 shows several views of an embodiment of an activation cam, lock element and a complementary lock element in accordance with the present invention; and FIGS. 8 to 11 are views of another embodiment of a needle safety module in accordance with the present invention.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc. It should be understood that any use herein of relative positional, directional or orientational terms is for convenience of description and is not intended to be limiting.

Figure 1:
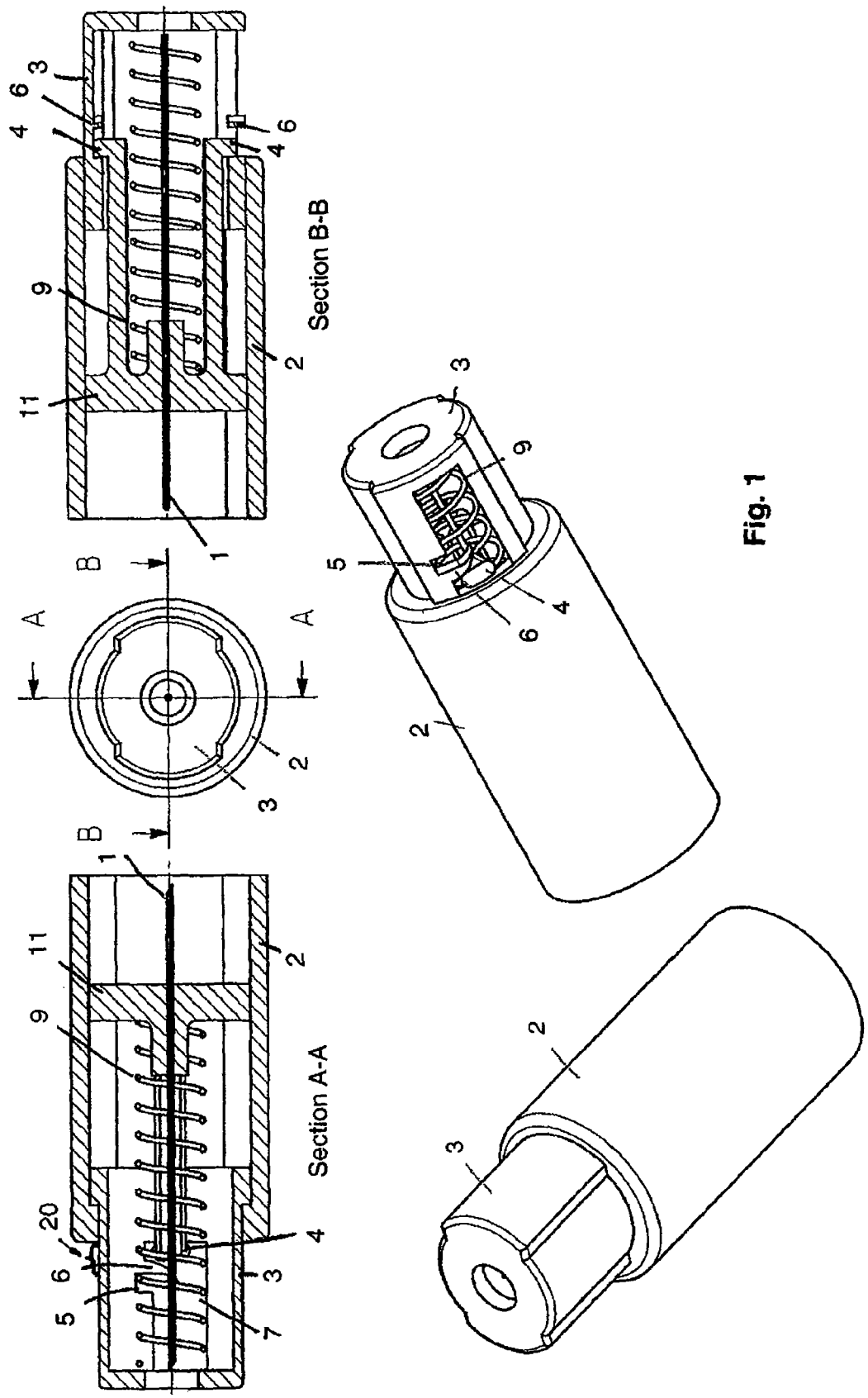
FIG. 1 shows several views of an embodiment of a needle safety module in accordance with the present invention.

FIG. 1 illustrates several views of a first embodiment of the present invention wherein a needle safety module comprises a housing 2 and a needle guard 3 mounted on it which is able to move along a needle 1. As illustrated in FIG. 1, the needle guard 3 is disposed in the initial position. The needle guard 3 is pushed in the distal (forward or front) direction and held in its initial position by a spring 9. The spring 9 is supported on a needle holder 11, which is connected to the housing 2 so that it can not move axially, and on a collar-shaped distal end of the needle guard 3 pointing toward the mid-axis. A lock element 4 is located in a groove 7, formed by the needle guard 3. In the perspective view shown on the right-hand side, the groove is provided in the form of an orifice. The groove may also be of a pocket-type shape rather than an orifice, as illustrated in the perspective view shown on the left-hand side of FIG. 1. The lock element 4 is integrally joined to the needle holder 11 via an arm in a flexible, e.g. elastically or resiliently deformable, manner. The needle holder 11 is connected to the housing 2 in a non-positive manner. Alternatively, the needle holder 11 could be connected to the housing by a positive fit or by its material, and/or may be of an integral design.

An activation cam 6 projects transversely to the direction of movement of the needle guard 3 into the groove 7. The activation cam 6 has an inclined region or convex shape at its surface pointing or extending in the proximal (rear or rearward) direction, which pushes the lock element 4 out transversely to the direction of movement of the needle guard 3, in this instance downward, as the needle guard 3 moves in the proximal direction. The needle guard 3 also forms a complementary lock element 5, which is laterally disposed outside of the alignment directed in the longitudinal direction and extending through the activation cam 6. The activation cam 6 has a curved shape in the distal direction and the activation cam 6 extends sufficiently far in a direction that it at least partially covers the complementary lock element 5, such that the lock element 4 cannot engage with the complementary lock element 5 when it is moved past the activation cam 6 and springs back in the direction from which the lock element 4 was moved out from the activation cam 6. In this state, the needle tip extends at least far enough out of the distal end of the needle guard 3 so that the needle tip at least touches the piercing point of the patient. This may be regarded and/or referred to as the activation position or injection position. If desired, the needle guard 3 can now be moved even farther in the proximal direction so that the needle 1 pierces the tissue even deeper. Once the injection has terminated, the needle 1 is pulled out of the body, as a result of which the spring 9 pushes the needle guard 3 in the distal direction. As this happens, the lock element 4, which is now disposed distally of the activation cam 6, is pushed into the complementary lock element 5 by the concavely oblique shape of the driving surface of the activation cam 6 pointing in the distal direction. In this position, the needle guard 3 is locked so that it is not able to move axially relative to the housing and if the needle safety module is used correctly can no longer be released.

Since the needle guard 3 is moved by a measured distance along the needle longitudinal axis in the end position in which the lock element 4 is disposed in the complementary lock element 5, an annular marking 20 extending around the circumference of the needle guard 3 in the region of the distal end of the housing 2 disappears in the housing. In particular, the marking 20 is covered by a housing 2. As a result the user of the device is able to tell that the needle safety module has been used and can not be used again. For example, an annular, circumferentially extending stripe of an appropriate colour such as green is used for the marking 20, and the stripe is preferably of a width and assumes an appropriate position such that the marking 20 is completely covered by the housing 2 when the needle guard 3 is in the end position.

Figure 3A:
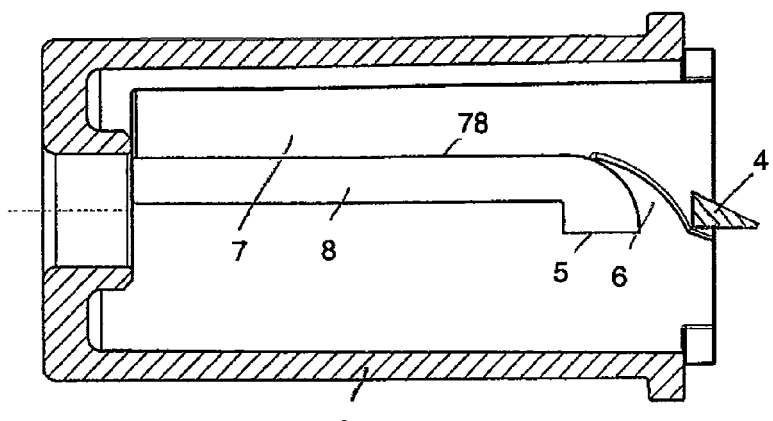
Figure 3B:
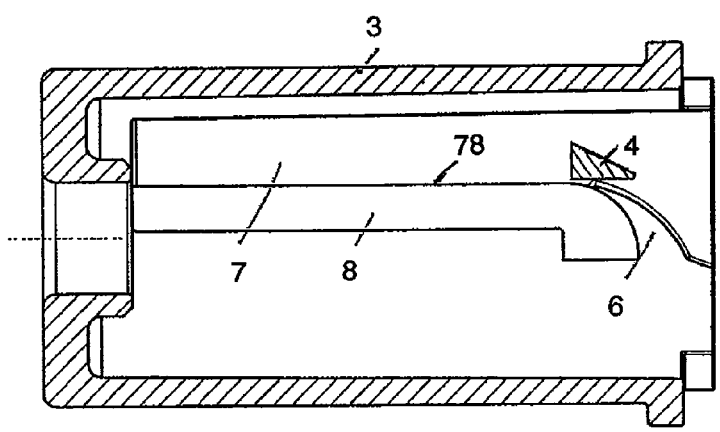
Figure 3C:
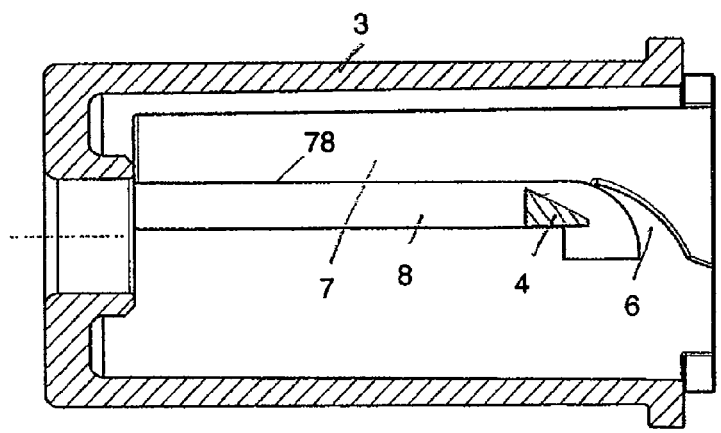
Figure 3D:
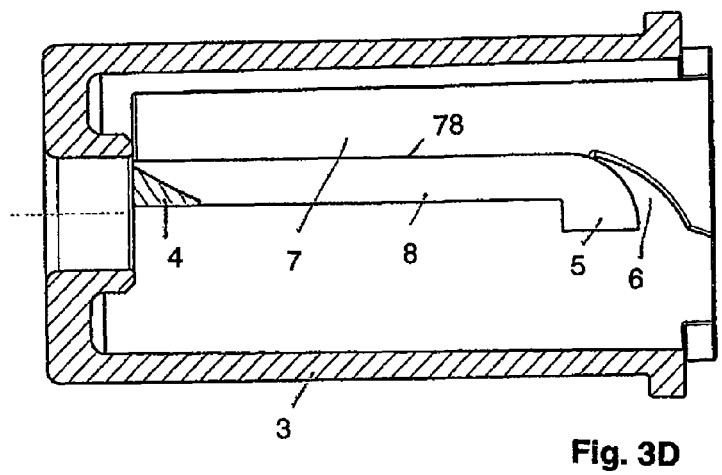
Figure 3E:
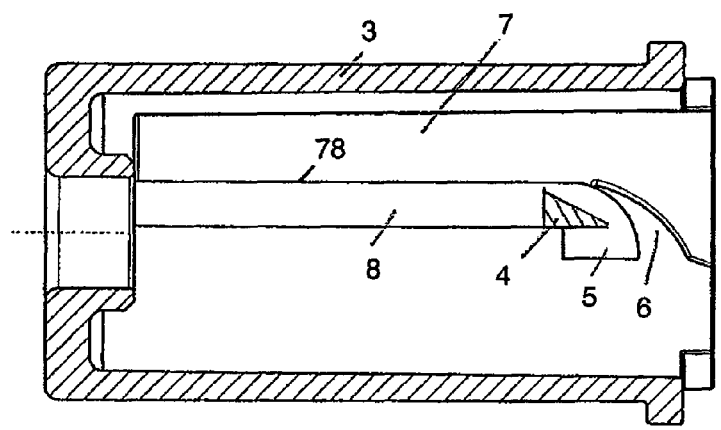
Figure 3F:
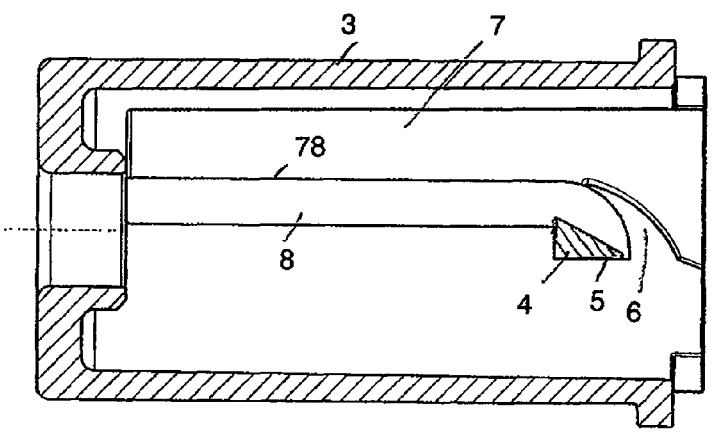

The embodiment of the needle safety module illustrated in FIGS. 2 to 3F has a modification compared with the embodiment illustrated in FIG. 1. The explanations given in connection with the embodiment of FIG. 1 therefore essentially apply to the embodiment illustrated in FIGS. 2 and 3. However, unlike the embodiment illustrated in FIG. 1, the needle guard 3 depicted in FIGS. 2 to 3F has a first groove 7 and a second groove 8. The first groove 7 has a groove base along which the lock element 4 slides as it is moved transversely by the lock cam 6 as the needle guard 3 moves out of the initial position in the proximal direction. In a position in which the lock element 4 has been moved past the lock cam 6, the lock element 4 latches in the second groove 8. As illustrated here, the second groove 8 may be an orifice or a groove 8 which also has a groove base, in which case the distance of the groove base of the first groove 7 from the needle longitudinal axis is shorter than the distance of the groove base of the second groove 8 from the needle longitudinal axis. In other words, there is a height offset between the first groove 7 and the second groove 8, which prevents the lock element 4 from sliding back from the second groove 8 into the first groove 7.

FIGS. 3A to 3F illustrate the needle guard 3 in section and the different positions of the lock element 4, which is illustrated without an arm and is shown only by the part which locates with the pawl system (which may be thought of as comprising elements 5, 6, 7, 8). FIG. 3a illustrates the initial position. The lock element 4 is axially aligned with the complementary lock element 5. Due to the resilient design of the lock element 4 on the arm, not illustrated, the lock element 4 tends to latch in the complementary lock element 5 due to its elasticity, provided it is in the corresponding axial position. In the arrangement illustrated in FIG. 3B, the needle guard 3 has moved in the proximal direction, causing the lock element 4 to be deflected transversely to the direction of movement due to the curved switching surface of the activation cam 6 pointing in the proximal direction. The lock element 4 may also slide along the groove base of the first groove 7. In FIG. 3C, the lock element 4 is illustrated in a position in which it has moved past the activation cam 6. This position may be termed the trigger or activation position which, to a certain extent, represents a special situation of the injection position because it is assumed that the needle tip (not illustrated) has made contact with the body tissue of the patient. When the lock element 4 is in the position illustrated in FIG. 3C, having moved past the activation cam 6, the lock element 4 has moved out of the first groove 7 and latched in the second groove 8 due to its resiliently elastic design. As a result of the shoulder 78, the lock element 4 is no longer able to move back into the first groove 7.

FIG. 3D illustrates the lock element 4 and the needle guard 3 in a position in which the needle is projecting out of the distal end of the needle guard 3 by its full injection length.

In FIG. 3E, the lock element 4 and the needle guard 3 are illustrated in a position in which the needle guard 3 has been moved back in the distal direction out of the injection position or trigger position. As this happens, the lock element 4 is able to move between the end of the activation cam 6 inclined in the distal direction and the complementary lock element 5, which was not possible during the movement from the position illustrated in FIG. 3B into the position illustrated in FIG. 3C. When the needle guard 3 is moved out of the position illustrated in FIG. 3E even farther in the distal direction, the lock element 4 latches in or with the complementary lock element 5 because of the resilient design of the lock element 4. In the position illustrated in FIG. 3F, the needle guard 3 is locked so that it is not able to move axially.

Figure 4:
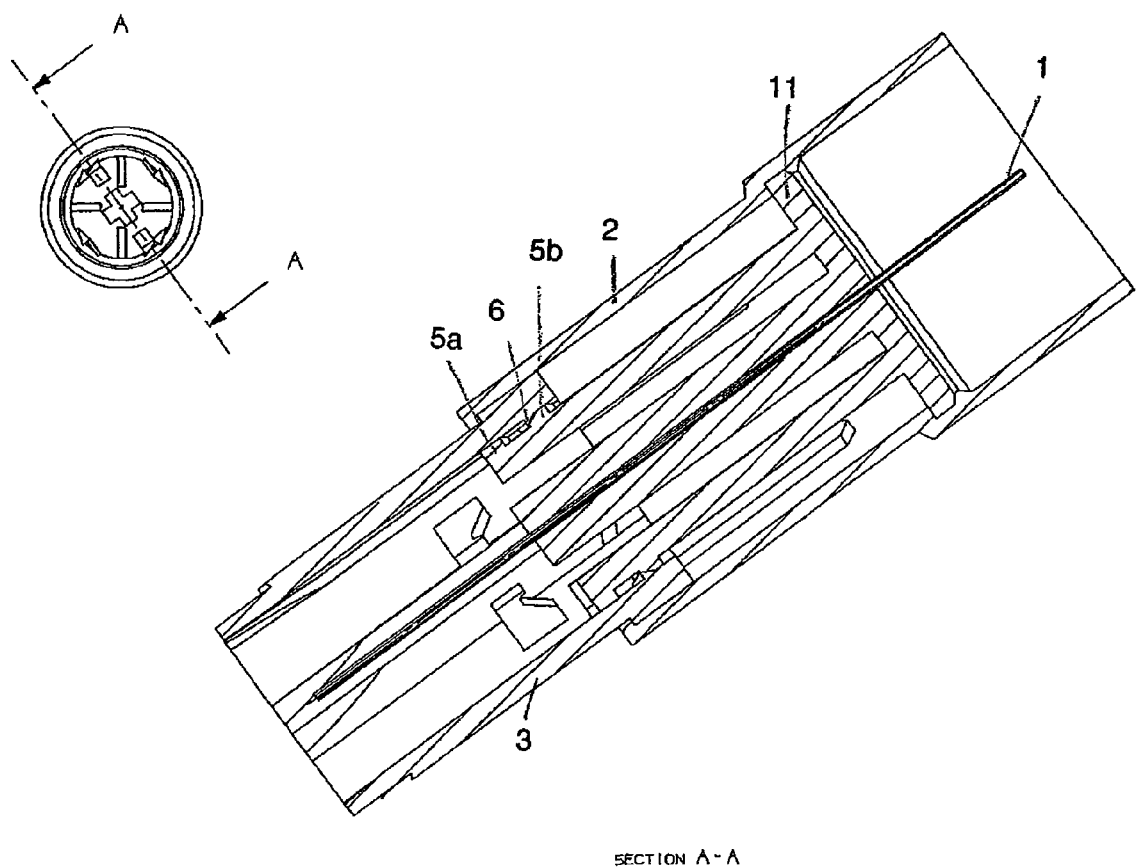
FIGS. 4 to 6E are views of another embodiment of a safety needle module in accordance with the present invention.
Figure 5:
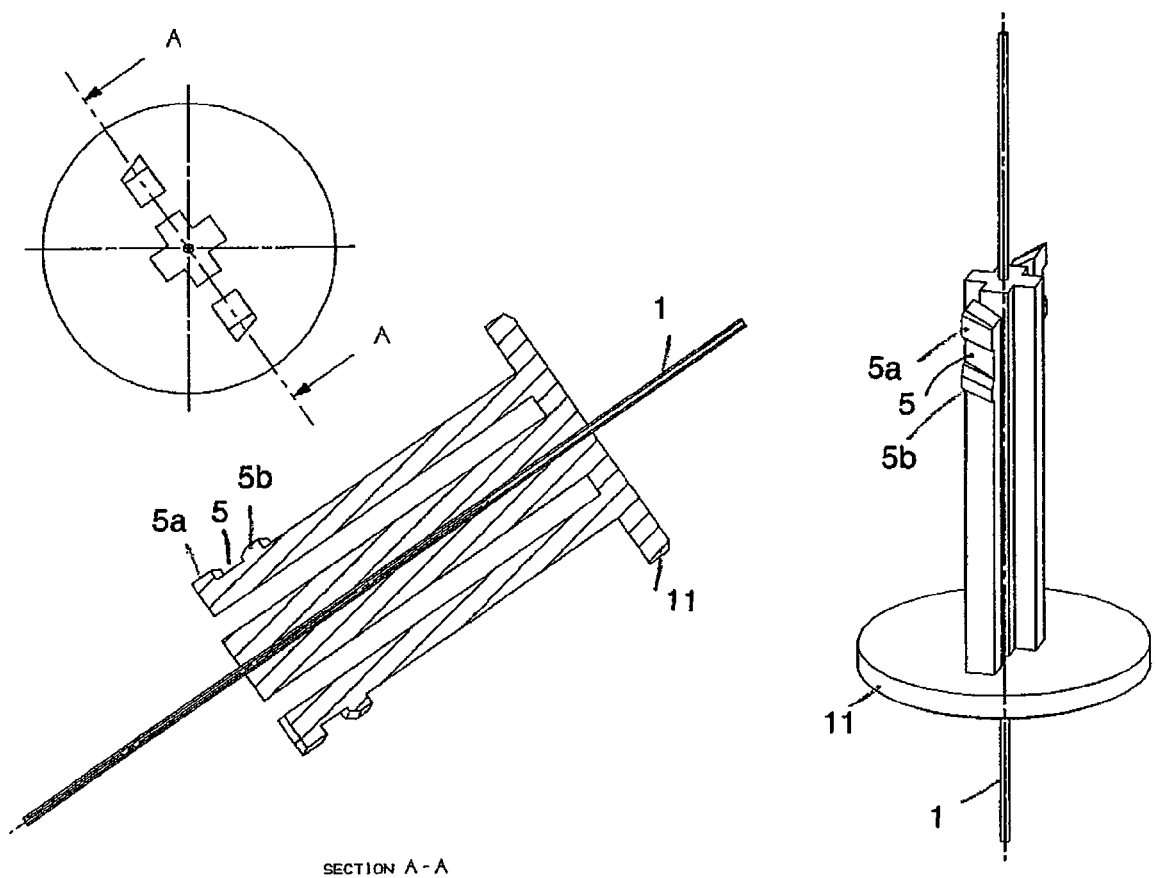

FIGS. 4 to 6E illustrate another embodiment of a needle safety module in accordance with the present invention. The needle safety module comprises a housing 2, in which a needle holder 11, which will be described in more detail with reference to FIG. 5, is accommodated by a positive catch connection. The needle holder 11 is used to mount an injection needle 1 so that it can not move axially. The needle 1 may be cast into the needle holder 11 by an injection moulding process. The needle holder 11 has two cams 5a, 5b joined to it with a recess formed between the cams 5a and 5b, which serves as the complementary lock element 5. The cams 5a and 5b are resiliently and, in some embodiments, integrally joined to the needle holder 11 via an arm. The housing 2 is fitted with a needle guard 3, which is able to move axially relative to the housing 2. The needle safety module illustrated in FIG. 4 shows the needle guard 3 in an initial position.

Figure 6A:
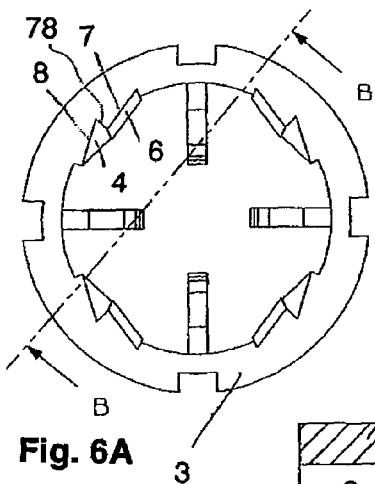

As may be seen from the perspective view illustrated in FIG. 5, the cams 5a and 5b are set at an angle with respect to the needle longitudinal axis. This angular set enables a transverse movement of the complementary lock element 5 or cams 5a and 5b in specific positions, as will be explained with reference to FIGS. 6A to 6E. FIG. 6A is a view of a needle guard 3 from the end. The needle guard 3 has four recesses in its external circumferential surface in which elements of the housing 2 are able to locate, thereby establishing an anti-rotation lock between the needle guard 3 and the housing 2. The needle guard 3 also has four inwardly directed projections, which serve as a stop for a spring element which is supported on the four projections of the needle guard 3 on the one hand and on the proximal end of the needle holder 11 on the other.

The needle guard 3 also has a first groove 7 and a second groove 8, each of which has a groove base, and the two groove bases are inclined at a tangent in the same direction. In other words, the groove bases of grooves 7 and 8 are inclined at a rolling angle about the longitudinal axis of the needle guard 3. A height offset 78 is formed due to the angular set between the grooves 7 and 8. The purpose of the offset 78 is to prevent the complementary lock element 5 from moving out of groove 8 into groove 7. Projecting out from the groove base of groove 7 into the interior of the guard is an activation cam 6. The activation cam 6 has a "saw-tooth" shape and its flatter side points in the proximal direction of the needle guard 3. Projecting out from the groove base of the second groove 8 is a lock element 4 directed toward the interior of the guard 3. The lock element 4 has a respective stop surface pointing in the proximal and in the distal direction which can not be overcome. The lock element 4 tapers across the width of the second groove 8 from the edge 78 to its oppositely lying edge.

Figure 6B:
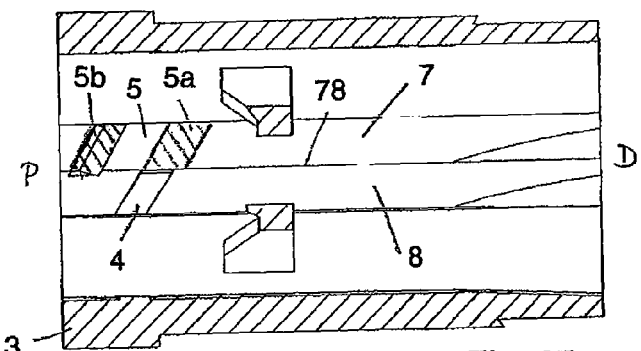

FIGS. 4 and 6B illustrate the positions of the activation cam 6, the complementary lock element 5, including the cams 5a and 5b, and the lock element 4 with the needle guard 3 in an initial position. At least the cam 5b is disposed proximally of the activation cam 6. The complementary lock element 5 is disposed in the first groove 7. As the needle guard 3 moves in the proximal direction, the complementary lock element 5, in particular the cam 5b, is moved past the activation cam 6 and assumes the position illustrated in FIG. 6C. During the latter movement, the complementary lock element 5, including the cams 5a and 5b, lifts out of the groove base of the first groove 7. Once the complementary lock element 5 has moved past the activation cam 6, it moves back into contact with the groove base of the first groove 7. Due to the saw-tooth design of the locking cam 6, in particular its stop surfaces pointing in the distal direction, the complementary lock element 5, in particular the cam 5b, can no longer be moved back across the activation cam 6 into the initial position.

Figure 6C:
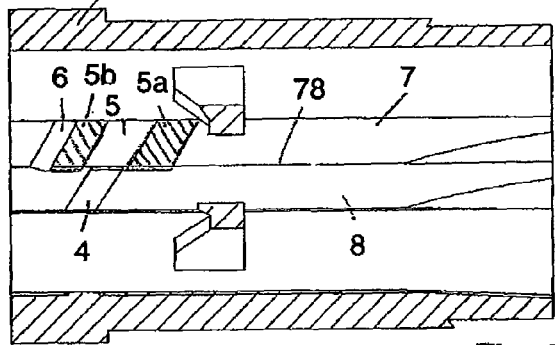
Figure 6D:
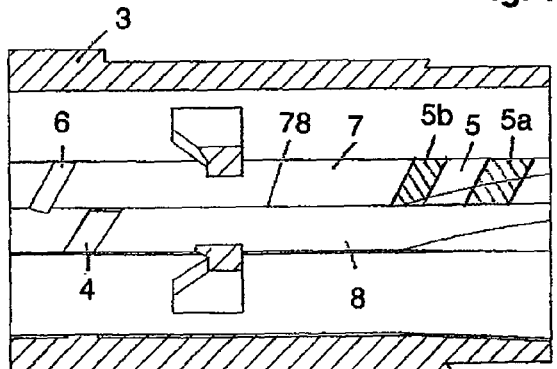
Figure 6E:
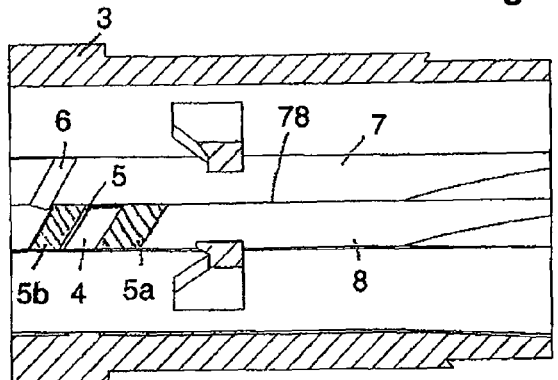
Figure 9:
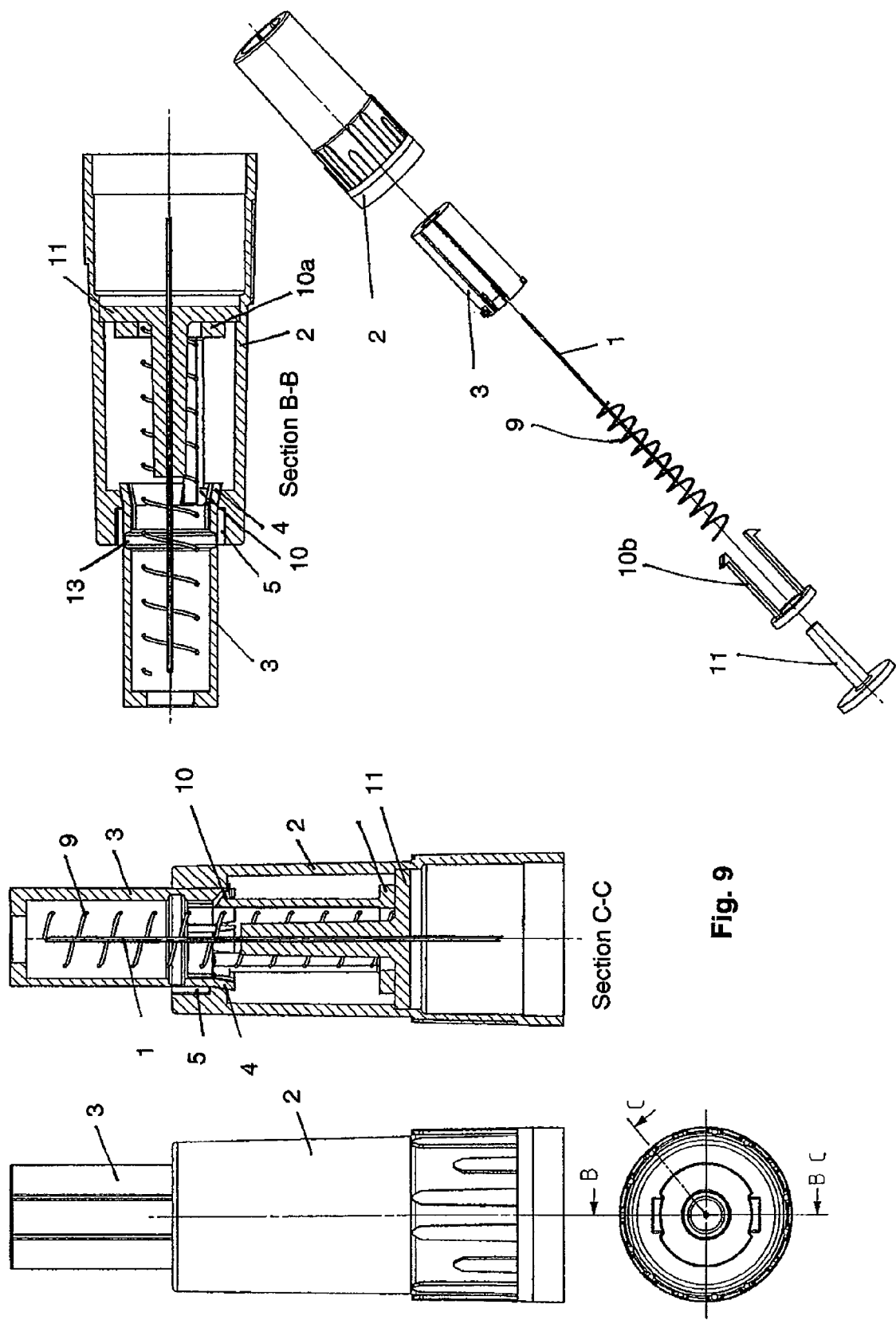

FIG. 6E illustrates the position of the complementary lock element 5 relative to the needle guard 3 in a position in which the needle has been extracted from the distal end of the needle guard by approximately its full injection length.

When the needle is pulled out of the tissue, the needle guard 3 is pushed back in the distal direction by the spring (not illustrated), causing the complementary lock element 5 to assume again the position illustrated in FIG. 6C.

When the needle guard 3 is moved out of the position illustrated in FIG. 6C even farther in the distal direction, for example by the spring, the complementary lock element 5 assumes the position illustrated in FIG. 6E. In other words, the complementary lock element 5 and the lock element 4 latch. In this position, the needle guard 3 can no longer be moved relative to the housing 2 because any movement of the complementary lock element 5 from the second groove 8 into the first groove 7 is prevented by the offset 78 and the stops of the lock element 4 pointing in the distal and proximal direction. The fact that the activation cam 6 is set at an angle with respect to the longitudinal axis and the lock element 4 is set at an angle with respect to the longitudinal axis, in conjunction with the spring force of the spring acting on the needle guard 3, causes the transverse movement of the complementary lock element 5 from the position illustrated in FIG. 6C into the position illustrated in FIG. 6E.

FIG. 7 illustrates an alternative embodiment of an activation cam 6 and a complementary lock element 5, comprising the cams 5a and 5b. The advantage of this embodiment is that the activation cam 6 simultaneously assumes the function of the lock element 4. The needle safety module illustrated in FIGS. 4 to 6 may be provided with the activation cam 6 and the complementary lock element 5 illustrated in FIG. 7. With an embodiment of this type, the groove 8 or offset 78 illustrated in FIG. 6b and the lock element 4 are dispensed with.

The activation cam is split into two parts and has a front part 6a pointing in the proximal direction which extends at an angle in the distal direction (FIG. 7B) so that a complementary lock element 5 a with co-operating complementary angled region (cam 5a) can be pushed sideways past the activation cam (which may be thought of as comprising elements 6; 4; 6a). The part 6a of the activation cam extends out from the base groove of the groove 7 by a shorter height than the remaining part of the activation cam (FIG. 7A).

As illustrated in FIGS. 7E to H, when the needle guard 3 is moved out of the initial position in the proximal direction, the complementary lock element 5 is pushed sideways past the activation cam (FIG. G) until it has moved past the complementary lock element 5 and assumes a lateral position in which it was disposed in its initial position (FIG. H). The needle guard 3 can then be moved farther in the proximal direction, and the needle 1 can be injected. When the needle 1 has been pulled out of the body, the needle guard 3 is pushed in the distal direction by the spring 9. Due to the design of the surface of the cam 5b pointing in the proximal direction of the complementary lock element 5 (FIG. 7C), namely a surface inclined at an angle with respect to the groove base of the groove 7, the complementary lock element 5 is able to move across the activation cam 6 to the degree that it latches with the other part of the activation cam projecting out from the groove base. As a result, an axial movement of the complementary lock element 5 and the activation cam, which also acts as a lock element, is no longer possible. Consequently, a movement of the needle guard 3 relative to the housing 2 is also no longer possible. The needle safety module is therefore finally locked.

Figure 10:
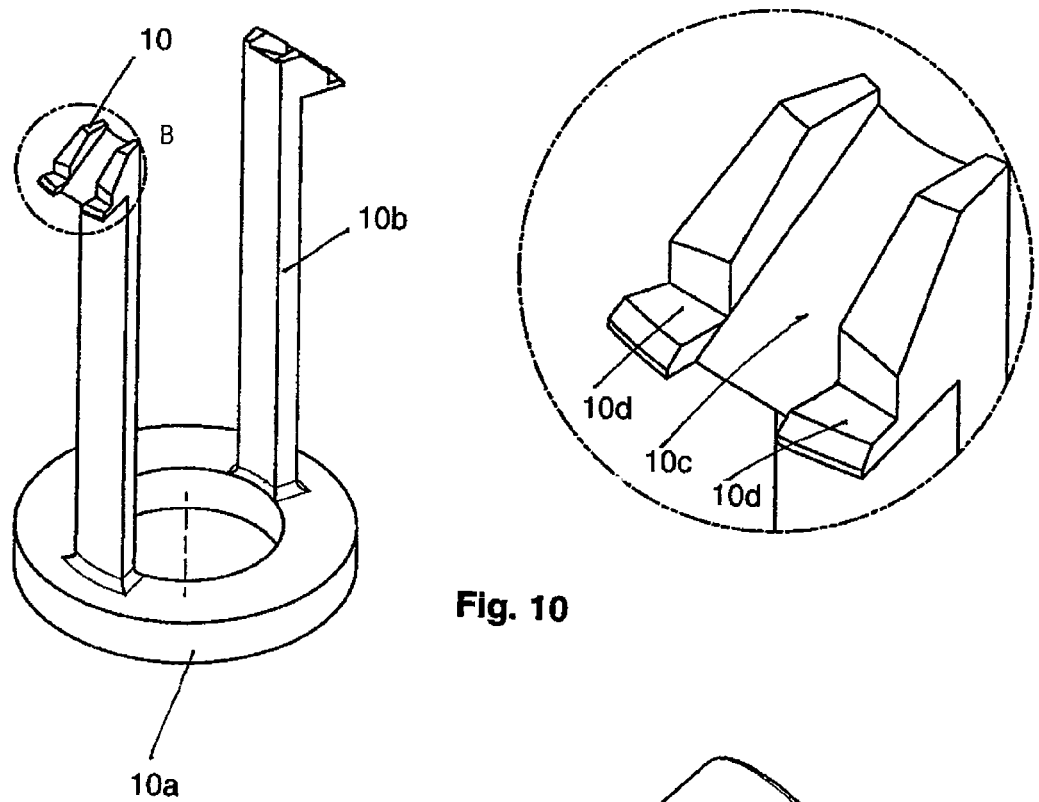
Figure 11:
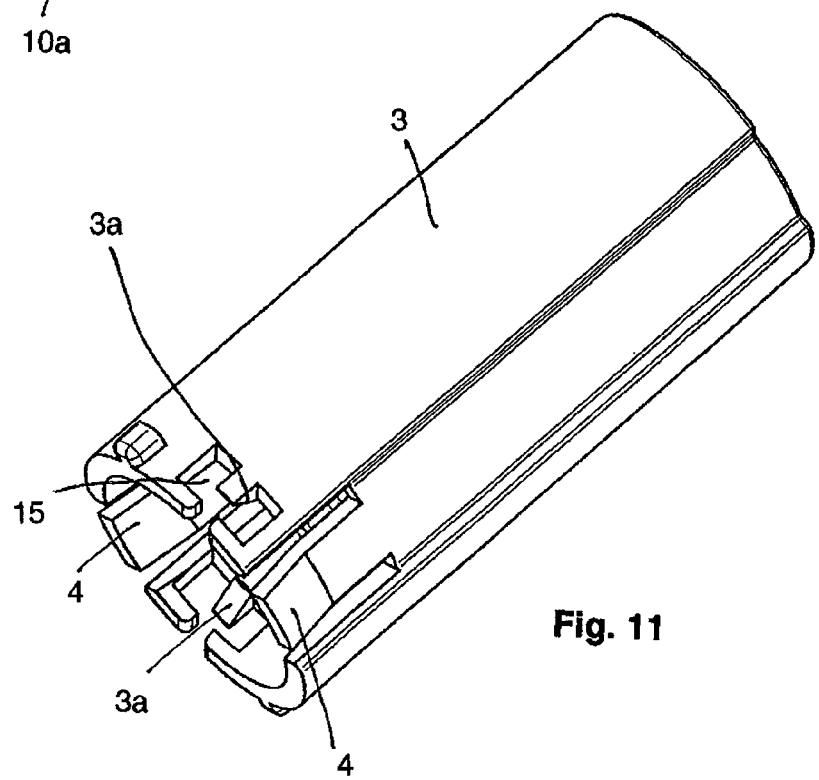

FIGS. 8 to 11 illustrate another embodiment of a needle module in accordance with the present invention, in which the needle guard 3 is disposed in end position distally of its initial position. The needle safety module has a housing 2, a needle guard 3 which is able to move axially relative to the housing 2 and a spring 9, which is supported on the needle holder 11 and the distal end of the needle guard 3 and pushes the needle guard 3 in the distal direction. The needle holder 11 is pressed into the housing 2 and holds an injection needle 1. The housing 2 has fixing means 12 by which the housing 2 can be attached to an injection device. The housing has a complementary lock element 5, in which the lock element 4 provided on the needle guard 3 is able to latch so that a movement of the needle guard 3 relative to the housing 2 is blocked when the lock element 4 is latched in the complementary lock element 5. In the arrangements illustrated in FIGS. 8 and 9, the needle guard 3 is in an initial position, namely a position in which the lock element 4 has still not latched in the complementary lock element 5. The needle safety module also has a locking element 10, which extends through an orifice 15 (FIG. 11) in the needle guard 3 and locates in a shoulder formed by the housing 2 so that the needle guard 3 can not be moved any farther in the distal direction. The locking element 10 is integrally joined to an annular base element 10a via resilient arm 10b (FIG. 10). The annular base element 10a sits loosely on the end face of the needle holder 11 pointing in the distal direction.

The locking element 10 also has a driving surface 10c extending at an angle with respect to the direction of movement of the needle guard 3. This driving surface 10c co-operates with a matching inclined driving surface 3a of the needle guard 3 so that a movement of the needle guard 3 in the distal direction causes the locking element 10 to move transversely to the direction of movement of the needle guard 3. As a result of this transverse movement of the locking element 10 caused by the needle guard 3 moving in the distal direction, the engagement of the lugs 10d of the locking element 10 laterally engaging round the driving surface 10c is released. In some preferred embodiments, at the instant the engagement of the locking element 10 with the housing 2 is released, the needle tip extends far enough out of the distal end that it at least touches the injection point of the patient. The needle guard 3 can now be moved as far as needed in the proximal direction to enable the needle to effect a piercing movement. When the needle guard has been moved out of this position back in the distal direction, the locking element 10 latches in the groove 13, as a result of which the locking element 10 is no longer able to effect an axial movement relative to the needle guard 3, at least in one direction, so that when the needle guard 3 is moved farther in the distal direction, the locking element 10, including the annular base element 10a and the arms 10b, is also driven in the distal direction. At the end of the movement in the distal direction, the lock element 4 latches in the complementary lock element 5, causing the needle guard 3 to be locked so that it can not be moved axially relative to the housing 2.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A needle safety module for attaching to an injection device for administering a liquid product, said needle safety module comprising:
   a) a housing;
   b) a needle connected to the housing such that the needle cannot move axially, the needle having a distal needle tip; and
   c) a needle guard having a distal end, which can be placed against an injection point via its distal end and moves axially and non-rotatably relative to the needle or to the housing from an initial position in which the distal needle tip is covered, to an injection position in which the distal needle tip extends far enough out of the needle guard that the distal needle tip at least touches the injection point, and to an end position in which the distal needle tip is covered; wherein
   d) the needle guard moves by a predefined movement in the distal or the proximal direction between the initial position and the end position; wherein
   e) the needle guard is locked such that it cannot move axially relative to the needle or to the housing upon movement from the injection position to the end position; and wherein
   f) a distance the needle guard moves from its initial position to its injection position differs from a distance the needle guard moves from its injection position to its end position.

2. The needle safety module according to claim 1, wherein the needle guard has a marking which can be seen when the needle guard is in the initial position or the end position.

3. The needle safety module according to claim 2, wherein if the marking can be seen in the initial position, then it is covered in the end position, and if the marking can be seen in the end position, then it is covered in the initial position.

4. The needle safety module according to claim 1, wherein the needle guard has a first marking which can be seen when the needle guard is in the initial position and a second marking which is different from the first marking and can be seen in the end position.

5. The needle safety module according to claim 4, wherein the second marking is covered when the needle guard is in the initial position, and the first marking is covered when the needle guard is in the end position.

6. A needle safety module for attaching to an injection device for administering a liquid product, said needle safety module comprising:
  a) a housing;
  b) a needle having a tip and connected to the housing such that it cannot move axially;
  c) a needle guard having a first end, said needle guard able to be placed against an injection point via its first end and moves axially and non-rotatably relative to the needle or to the housing from an initial position in which the needle tip is covered, via an injection position in which the needle tip extends far enough out of the needle guard that the needle tip at least touches the injection point, and into an end position in which the needle tip is covered; and
  d) a lock comprising a lock element is formed on one of the needle guard and the housing and a complementary lock element formed on the other of the needle guard and the housing;
  e) wherein the needle guard moves by a predefined movement in the distal or the proximal direction between the initial position and the end position;
  f) wherein as the needle guard moves from the initial position to the injection position, the lock element or the complementary lock element formed on the housing changes position relative to the needle guard and prevents the needle guard from moving from the injection position back into the initial position; and
  g) wherein upon the needle guard moving from the injection position to the end position, the lock element latches into the complementary lock element due to the changed position of the lock element or the complementary lock element formed on the housing such that the needle guard is locked and prevented from moving axially relative to the needle or the housing.

7. The needle safety module according to claim 6, wherein the lock element is a projection and the complementary lock element is a recess formed between two projections.

8. The needle safety module according to claim 6, further comprising an activation cam, wherein when the needle guard moves out of the initial position, the lock element or the complementary lock element is pushed by the activation cam transversely with respect to the direction of movement, such that the lock element or the complementary lock element can be moved past the activation cam.

9. The needle safety module according to claim 8, wherein the lock element or the complementary lock element snaps back in the direction from which it was deflected by the activation cam, once it has moved past the activation cam.

10. The needle safety module according to claim 9, wherein the activation cam is disposed at an axial position such that the lock element or the complementary lock element is moved past the activation cam at the latest when the needle tip is able to touch the injection point.

11. The needle safety module according to claim 10, wherein the activation cam is shaped such that when the needle guard moves out of a position in which the lock element or the complementary lock element has moved past the activation cam, the lock element or complementary lock element is pushed by the activation cam transversely with respect to the direction of movement of the needle guard.

12. The needle safety module according to claim 11, wherein the transverse movement with respect to the direction of movement causes the lock element and complementary lock element to engage.

13. The needle safety module according to claim 12, wherein the transverse movement with respect to the direction of movement is a movement of the needle guard or the housing in at least one of a radial direction, a circumferential direction or at a tangent to the circumferential direction.

14. The needle safety module according to claim 13, wherein the activation cam acts as a lock element and the complementary lock element latches into the activation cam.

15. The needle safety module according to claim 13, wherein the lock element or the complementary lock element is disposed out of an alignment extending in the direction of movement of the needle guard and passing through the activation cam.

16. The needle safety module according to claim 6, further comprising a locking element which can be moved relative to the housing and the needle guard and engages with the needle guard and the housing in the initial position and prevents a movement of the needle guard.

17. The needle safety module according to claim 16, wherein the needle guard is shaped such that when the needle guard moves, the locking element is moved at least out of engagement with the housing, whereby the needle guard can be moved into the end position.

18. The needle safety module according to claim 17, wherein the locking element can be moved transversely with respect to the direction of movement of the needle guard.

19. The needle safety module according to claim 18, wherein the locking element latches with the needle guard once it has moved out of engagement with the housing, wherein the locking element is at least partially slaved in the movement of the needle guard.

20. The needle safety module according to claim 2, wherein the marking comprises a width corresponding to the axial distance between the initial position and the end position of the needle guard, such that in the initial position, the marking is visible from a distal end of the housing, and in the end position, the marking is recessed within the housing.

* * * * *